United States Patent [19]
Holmes-Farley et al.

[11] Patent Number: 6,083,495
[45] Date of Patent: *Jul. 4, 2000

[54] METHOD OF MAKING PHOSPHATE-BINDING POLYMERS FOR ORAL ADMINISTRATION

[75] Inventors: Stephen Randall Holmes-Farley, Arlington; W. Harry Mandeville, III, Lynnfield; George M. Whitesides, Newton, all of Mass.

[73] Assignee: GelTex Pharmaceuticals, Inc., Waltham, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/929,784

[22] Filed: Sep. 15, 1997

Related U.S. Application Data

[60] Division of application No. 08/471,747, Jun. 6, 1995, Pat. No. 5,667,775, which is a continuation-in-part of application No. 08/238,458, May 5, 1994, Pat. No. 5,496,545, which is a continuation-in-part of application No. 08/105,591, Aug. 11, 1993, abandoned.

[51] Int. Cl.$^7$ .............................. A61K 9/14; A61K 31/785
[52] U.S. Cl. .................. 424/78.1; 424/78.01; 424/78.08; 424/78.11; 424/78.12; 424/489
[58] Field of Search ...................... 424/78.11, 489, 424/78.08, 78.1, 78.01, 78.12

[56] References Cited

U.S. PATENT DOCUMENTS

| | | | |
|---|---|---|---|
| 2,456,428 | 12/1948 | Parker | 260/80 |
| 4,504,640 | 3/1985 | Harada et al. | 526/193 |
| 4,605,701 | 8/1986 | Harada et al. | 525/107 |
| 4,895,621 | 1/1990 | Hassler | 162/164.3 |

*Primary Examiner*—James M. Spear
*Attorney, Agent, or Firm*—Hamilton, Brook, Smith & Reynolds, P.C.

[57] ABSTRACT

Phosphate-binding polymers are provided for removing phosphate from the gastrointestinal tract. The polymers are orally administered, and are useful for the treatment of hyperphosphatemia.

8 Claims, 2 Drawing Sheets

METHOD OF MAKING PHOSPHATE-BINDING POLYMERS FOR ORAL ADMINISTRATION

RELATED APPLICATION

This application is a division of application Ser. No. 08/471,747 filed Jun. 6, 1995 U.S. Pat. No. 5,667,775 which is a continuation-in-part of U.S. Ser. No. 08/238,458 filed May 5, 1994, now U. S. Pat. No. 5,496,545, which is a continuation-in-part of U.S. Ser. No. 08/105,591, filed Aug. 11, 1993, now abandoned.

BACKGROUND OF THE INVENTION

Hyperphosphatemia frequently accompanies diseases associated with inadequate renal function, hypoparathyroidism, and certain other medical conditions. Hyperphosphatemia is typically defined as possessing a serum phosphate levels of over about 6 mg/dL. The condition, especially if present over extended periods of time, leads to severe abnormalities in calcium and phosphorus metabolism and can be manifested by aberrant calcification in joints, lungs, and eyes.

Therapeutic efforts to reduce serum phosphate include dialysis, reduction in dietary phosphate, and oral administration of insoluble phosphate binders to reduce gastrointestinal absorption. Dialysis and reduced dietary phosphate are generally unsuccessful in adequately reversing hyperphosphatemia. Further difficulties in these therapeutic regimens include the invasive nature of dialysis and the difficulties in modifying dietary habits in the latter therapy.

The oral administration of certain phosphate binders has also been suggested. Phosphate binders include calcium or aluminum salts. Calcium salts have been widely used to bind intestinal phosphate and prevent absorption. The ingested calcium combines with phosphate to form insoluble calcium phosphate salts such as $Ca_3(PO_4)_2$, $CaHPO_4$, or $Ca(H_2PO_4)_2$. Different types of calcium salts, including calcium carbonate, acetate (such as PhosLo® calcium acetate tablets), citrate, alginate, and ketoacid salts have been utilized for phosphate binding. This class of therapeutics generally results in hypercalcemia due from absorption of high amounts of ingested calcium. Hypercalcemia has been indicated in many serious side effects, such as cardiac arrhythmias, renal failure, and skin and visceral calcification. Frequent monitoring of serum calcium levels is required during therapy with calcium-based phosphate binders.

Aluminum-based phosphate binders, such as Amphojel® aluminum hydroxide gel, have also been used for treating hyperphosphatemia. These compounds complex with intestinal phosphate to form highly insoluble aluminum phosphate; the bound phosphate is unavailable for absorption by the patient. Prolonged use of aluminum gels leads to accumulations of aluminum, and often to aluminum toxicity, accompanied by such symptoms as encephalopathy, osteomalacia, and myopathy.

Selected ion exchange resins have also been suggested for use in binding phosphate. Those tested include Dowex® anion-exchange resins in the chloride form, such as XF 43311, XY 40013, ˙XF 43254, XY 40011, and XY 40012. These resins have several drawbacks for treatment of hyperphosphatemia, including poor binding efficiency, necessitating use of high dosages for significant reduction of absorbed phosphate.

Thus a need exists for improved phosphate binders which can be administered orally in acceptable dosage levels without resulting in many of the serious side effects discussed above.

SUMMARY OF THE INVENTION

The invention relates to the discovery that a class of anion exchange polymers have improved phosphate binding properties. In general, the invention features a method of removing phosphate from a patient by ion exchange, which involves oral administration of a therapeutically effective amount of a composition containing at least one phosphate-binding polymer. The polymers of the invention may be crosslinked with a crosslinking agent.

The invention provides an effective treatment for decreasing the serum level of phosphate by binding phosphate in the gastrointestinal tract, without comcomittantly increasing the absorption of any clinically undesirable materials, particularly calcium or aluminum.

Other features and advantages will be apparent from the following description of the preferred embodiments and from the claims.

DESCRIPTION OF THE INVENTION

Figure 1:
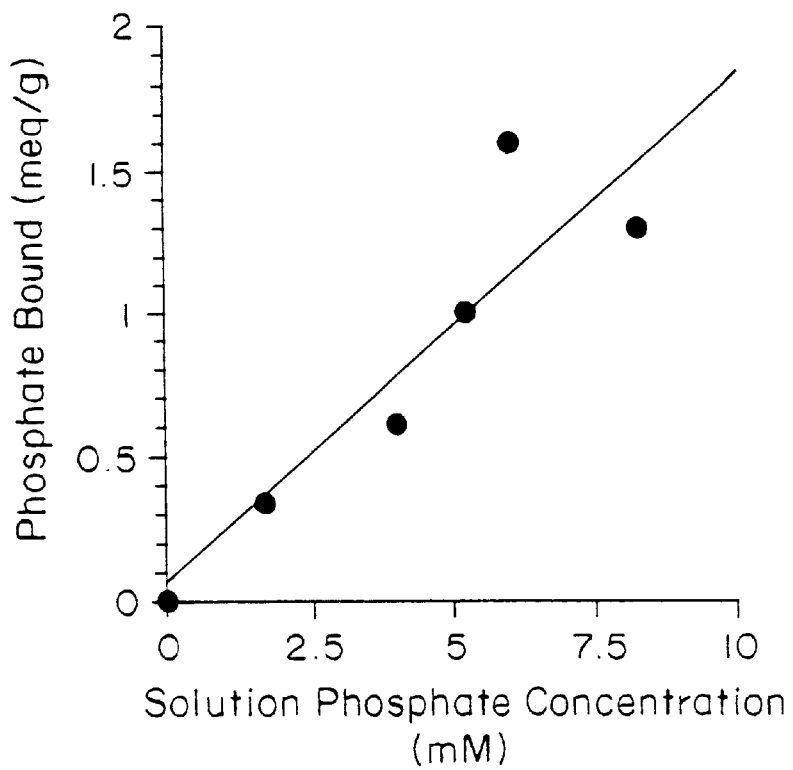
FIG. 1 is an illustration of the bound phosphate relevant to solution phosphate concentration after a phosphate solution is treated with poly(dimethyl-aminopropylacrylamide).

The polymers of the invention generally include hydrophilic anion exchange resins, particularly aliphatic amine polymers. The "amine" group can be present in the form of a primary, secondary or tertiary amine, quaternary ammonium salt, amidine, guanadine, hydrazine, or combinations thereof. The amine can be within the linear structure of the polymer (such as in polyethylenimine or a a condensation polymer of a polyaminoalkane, e.g. diethylenetriamine, and a crosslinking agent, such as epichlorohydrin) or as a functional group pendant from the polymer backbone (such as in polyallylamine, polyvinylamine or poly(aminoethyl)acrylate).

In one aspect, the polymer is characterized by a repeating unit having the formula

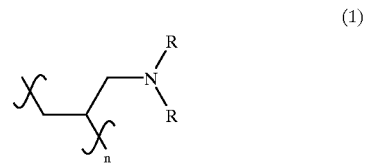

(1)

or a copolymer thereof, wherein n is an integer and each R, independently, is H or a substituted or unsubstituted alkyl, such as a lower alkyl (e.g., having between 1 and 5 carbon atoms, inclusive), alkylamino (e.g., having between 1 and 5 carbons atoms, inclusive, such as ethylamino) or aryl (e.g., phenyl) group.

In a second aspect, the polymer is characterized by a repeating unit having the formula

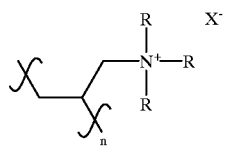

(2)

or a copolymer thereof, wherein n is an integer, each R, independently, is H or a substituted or unsubstituted alkyl (e.g., having between 1 and 5 carbon atoms, inclusive), alkylamino (e.g., having between 1 and 5 carbons atoms, inclusive, such as ethylamino) or aryl (e.g., phenyl) group, and each $X^-$ is an exchangeable negatively charged counterion.

One example of a copolymer according to the second aspect of the invention is characterized by a first repeating unit having the formula

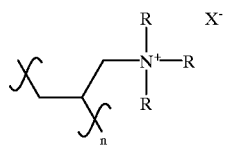

(2)

wherein n is an integer, each R, independently, is H or a substituted or unsubstituted alkyl (e.g., having between 1 and 5 carbon atoms, inclusive), alkylamino (e.g., having between 1 and 5 carbons atoms, inclusive, such as ethylamino) or aryl group (e.g., phenyl), and each $X^-$ is an exchangeable negatively charged counterion; and further characterized by a second repeating unit having the formula

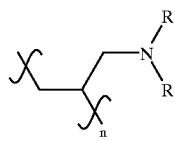

(3)

wherein each n, independently, is an integer and each R, independently, is H or a substituted or unsubstituted alkyl (e.g., having between 1 and 5 carbon atoms, inclusive), alkylamino (e.g., having between 1 and 5 carbons atoms, inclusive, such as ethylamino) or aryl group (e.g., phenyl).

In a fourth aspect, the polymer is characterized by a repeating unit having the formula

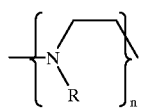

(4)

or a copolymer thereof, wherein n is an integer, and R is H or a substituted or unsubstituted alkyl (e.g., having between 1 and 5 carbon atoms, inclusive), alkylamino (e.g., having between 1 and 5 carbons atoms, inclusive, such as ethylamino) or aryl group (e.g., phenyl).

One example of a copolymer according to the second aspect of the invention is characterized by a first repeating unit having the formula

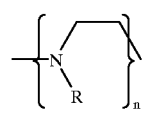

(4)

wherein n is an integer, and R is H or a substituted or unsubstituted alkyl (e.g., having between 1 and 5 carbon atoms, inclusive), alkylamino (e.g., having between 1 and 5 carbons atoms, inclusive, such as ethylamino) or aryl group (e.g., phenyl); and further characterized by a second repeating unit having the formula

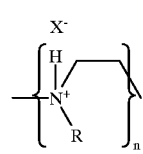

(5)

wherein each n, independently, is an integer and R is H or a substituted or unsubstituted alkyl (e.g., having between 1 and 5 carbon atoms, inclusive), alkylamino (e.g., having between 1 and 5 carbon atoms, inclusive, such as ethylamino) or aryl group (e.g., phenyl).

In a fifth aspect, the polymer is characterized by a repeating group having the formula

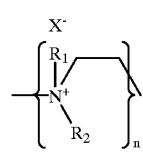

(6)

or a copolymer thereof, wherein n is an integer, and each $R_1$ and $R_2$, independently, is H or a substituted or unsubstituted alkyl (e.g., having between 1 and 5 carbon atoms, inclusive), and alkylamino (e.g., having between 1 and 5 carbons atoms, inclusive, such as ethylamino) or aryl group (e.g., phenyl), and each $X^-$ is an exchangeable negatively charged counterion.

In one preferred polymer according to the fifth aspect of the invention, at least one of the R groups is a hydrogen atom.

In a sixth aspect, the polymer is characterized by a repeat unit having the formula

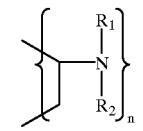

(7)

or a copolymer thereof, where n is an integer, each $R_1$ and $R_2$, independently, is H, a substituted or unsubstituted alkyl group containing 1 to 20 carbon atoms, an alkylamino group (e.g., having between 1 and 5 carbons atoms, inclusive, such as ethylamino), or an aryl group containing 6 to 12 atoms (e.g., phenyl).

In a seventh aspect, the polymer is characterized by a repeat unit having the formula

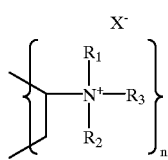

(8)

or a copolymer thereof, wherein n is an integer, each $R_1$, $R_2$ and $R_3$, independently, is H, a substituted or unsubstituted alkyl group containing 1 to 20 carbon atoms, an alkylamino group (e.g., having between 1 and 5 carbons atoms, inclusive, such as ethylamino), or an aryl group containing 6 to 12 atoms (e.g., phenyl), and each $X^-$ is an exchangeable negatively charged counterion.

In each case, the R groups can carry one or more substituents. Suitable substituents include therapeutic anionic groups, e.g., quaternary ammonium groups, or amine groups, e.g., primary and secondary alkyl or aryl amines. Examples of other suitable substituents include hydroxy, alkoxy, carboxamide, sulfonamide, halogen, alkyl, aryl, hydrazine, guanadine, urea, and carboxylic acid esters, for example.

The polymers are preferably crosslinked, in some cases by adding a crosslinking agent to the reaction mixture during or after polymerization. Examples of suitable crosslinking agents are diacrylates and dimethacrylates (e.g., ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate, polyethyleneglycol diacrylate), methylene bisacrylamide, methylene bismethacrylamide, ethylene bisacrylamide, epichlorohydrin, epibromohydrin, toluene diisocyanate, ethylenebismethacrylamide, ethylidene bisacrylamide, divinyl benzene, bisphenol A dimethacrylate, bisphenol A diacrylate, 1,4 butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, acryloyl chloride, or pyromellitic dianhydride.

The amount of crosslinking agent is typically between about 0.5 and about 75 weight %, and preferably between about 1 and about 25% by weight, based upon the combined weight of crosslinking and monomer. In another embodiment, the crosslinking agent is present between about 2 and about 20% by weight of polymer.

In some cases the polymers are crosslinked after polymerization. One method of obtaining such crosslinking involves reaction of the polymer with difunctional crosslinkers, such as epichlorohydrin, succinyl dichloride, the diglycidyl ether of bisphenol A, pyromellitic dianhydride, toluence diisocyanate, and ethylenediamine. A typical example is the reaction of poly(ethyleneimine) with epichlorohydrin. In this example the epichlorohydrin (1 to 100 parts) is added to a solution containing polyethyleneimine (100 parts) and heated to promote reaction. Other methods of inducing crosslinking on already polymerized materials include, but are not limited to, exposure to ionizing radiation, ultraviolet radiation, electron beams, radicals, and pyrolysis.

Examples of preferred crosslinking agents include epichlorohydrin, 1,4 butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate, toluene diisocyanate, acryloyl chloride, and pyromellitic dianhydride.

The negatively charged counterions, $X^-$, can be organic ions, inorganic ions, or a combination thereof. The inorganic ions suitable for use in this invention include halide (especially chloride), carbonate, bicarbonate, sulfate, bisulfate, hydroxide, nitrate, persulfate and sulfite. Suitable organic ions include acetate, ascorbate, benzoate, citrate, dihydrogen citrate, hydrogen citrate, oxalate, succinate, tartrate, taurocholate, glycocholate, and cholate.

In a preferred embodiment, the counterion does not have a detrimental side effect to the patient but rather is selected to have a therapeutic or nutritional benefit to the patient.

EXAMPLES

Candidate polymers were tested by stirring them in a phosphate containing solution at pH 7 for 3 hours. The solution was designed to mimic the conditions present in the small intestine.

| Solution Contents |
|---|
| 10–29 mM phosphate |
| 80 mM Sodium Chloride |
| 30 mM Sodium Carbonate |

The pH was adjusted to pH 7, once at the start of the test and again at the end of the test, using either aqueous NaOH or HCl. After 3 hours the polymer was filtered off and the residual phosphate concentration in the test solution was determined spectrophotometrically. The difference between the initial phosphate concentration and the final concentration was used to determine the amount of phosphate bound to the polymer. This result is expressed in milliequivalents per gram of starting polymer (meq/g).

Table 1 below shows the results obtained for several polymers. Higher numbers indicate a more effective polymer.

TABLE 1

| Polymer | Phosphate Bound (meq/g)* |
|---|---|
| Poly(allylamine/epichlorohydrin) | 3.1 |
| Poly(allylamine/butanediol diglycidyl ether) | 2.7 |
| Poly(allylamine/ethanediol diglycidyl ether) | 2.3 |
| Poly(allyltrimethylammonium chloride) | 0.3 |
| Poly(ethyleneimine)/acryloyl chloride | 1.2 |
| Polyethyleneimine "C" | 2.7 |
| Polyethyleneimine "A" | 2.2 |
| Poly(DET/EPI) | 1.5 |
| Polyethyleneimine "B" | 1.2 |
| Poly(dimethylaminopropylacrylamide) | 0.8 |
| Poly(PEH/EPI) | 0.7 |
| Poly(trimethylammoniomethyl styrene chloride) | 0.7 |
| Poly(pentaethylenehexaminemethacrylamide) | 0.7 |
| Poly(tetraethylenepentaminemethacrylamide) | 0,7 |
| Poly(diethylenetriaminemethacrylamide) | 0.5 |
| Poly(triethylenetetraminemethacrylamide) | 0.5 |
| Poly(aminoethylmethacrylamide) | 0.4 |
| Poly(vinylamine) | 0.4 |
| Poly(MAPTAC) | 0.24 |
| Poly(methylmethacrylate/PEI) | 0.2 |
| Poly(dimethylethyleneimine chloride) | 0.2 |
| Poly(diethylaminopropylmethacrylamide) | 0.1 |
| Poly(guanidinoacrylamide) | 0.1 |
| Poly(guanidinobutylacrylamide) | 0.1 |
| Poly(guanidinobutylmethacrylamide) | 0.1 |

*The values apply when the residual solution phosphate levels are ~5 mM.

Table 2 shows results obtained using various other materials to bind phosphate.

TABLE 2

| Polymer | Phosphate Bound (meq/g)* |
|---|---|
| Calcium Chloride | 4.0 |
| Calcium Lactate | 2.4 |
| Ox-Absorb ® | 0.5 |
| Maalox Plus ® | 0.3 |
| Sephadex DEAE A-25, 40–125 m | 0.2 |
| Aluminum Hydroxide, Dried Gel | 0.2 |

*The values apply when the residual solution phosphate levels are ~5 mM.

Table 3 shows results obtained for a variety of salts made from polyethyleneimine and organic and inorganic acids.

TABLE 3

| Polymer | Phosphate Bound (meq/g)* |
|---|---|
| Poly(ethyleneimine sulfate A) | 0.9 |
| Poly(ethyleneimine sulfate B) | 1.2 |
| Poly(ethyleneimine sulfate C) | 1.1 |
| Poly(ethyleneimine sulfate D) | 1.7 |
| Poly(ethyleneimine tartrate A) | 0.7 |
| Poly(ethyleneimine tartrate B) | 0.9 |
| Poly(ethyleneimine tartrate C) | 1.1 |
| Poly(ethyleneimine ascorbate A) | 0.55 |
| Poly(ethyleneimine ascorbate B) | 0.65 |
| Poly(ethyleneimine ascorbate C) | 0.9 |
| Poly(ethyleneimine citrate A) | 0.7 |
| Poly(ethyleneimine citrate B) | 1.0 |
| Poly(ethyleneimine citrate C) | 0.9 |
| Poly(ethyleneimine succinate A) | 1.1 |
| Poly(ethyleneimine succinate B) | 1.3 |
| Poly(ethyleneimine chloride) | 1.1 |

*The values apply when the residual solution phosphate levels are ~5 mM.

Oxabsorb® is an organic polymer that encapsulates calcium such that the calcium is available to bind to such ions as phosphate, but may not be released by the polymer and thus is not supposed to be absorbed by the patient.

The amount of phosphate bound by all of these materials, both polymers and inorganic gels, is expected to vary as the phosphate concentration varies. The graph FIG. 1 below shows the relationship between the solution phosphate concentration and the amount of phosphate bound to poly (dimethylaminopropylacrylamide). Other polymers of the class are expected to show a similar relationship.

In an alternate type of test, the polymer was exposed to an acidic environment prior to exposure to phosphate as might happen in a patient's stomach. The solid (0.1 g) was suspended in 40 mL of 0.1 M NaCl. This mixture was stirred for 10 minutes, and the pH was adjusted to 3.0 with 1 M HCl, and the mixture was stirred for 30 minutes. The mixture was centrifuged, the supernatant decanted, and the solid resuspended in 40 mL of 0.1 m NaCl. This mixture was stirred for 10 minutes, the pH was adjusted to 3.0 with 1 M HCl, and the mixture was stirred for 30 minutes. The mixture was centrifuged, the supernatant decanted, and the solid residue used in the usual phosphate assay. Results are shown in Table 4 for a variety of polymers and for aluminum hydroxide dried gel. In most cases the values for the amount of phosphate bound are higher in this test than in the usual assay.

TABLE 4

| Polymer | Phosphate Bound (meq/g)* |
|---|---|
| Poly(ethyleneimine sulfate B) | 1.2 |
| Poly(ethyleneimine sulfate C) | 1.3 |
| Poly(ethyleneimine tartrate B) | 1.3 |
| Poly(ethyleneimine tartrate C) | 1.4 |
| Poly(ethyleneimine ascorbate B) | 1.0 |
| Poly(ethyleneimine ascorbate C) | 1.0 |
| Poly(ethyleneimine citrate B) | 1.0 |
| Poly(ethyleneimine citrate C) | 1.3 |
| Poly(ethyleneimine succinate A) | 1.1 |
| Poly(ethyleneimine succinate B) | 1.3 |
| Poly(ethyleneimine chloride) | 1.4 |
| Aluminum Hydroxide | 0.7 |

*The values apply when the residual solution phosphate levels are ~5 mM.

Rat Dietary Phosphorus Excretion Model

Six 6–8 week old Sprague-Dawley rats were placed in metabolic cages and fed semi-purified rodent® chow powder containing 0.28% inorganic phosphorus. The diets were supplemented with 1.7% poly(allylamine/epichlorohydrin) or micro-crystalline cellulose; the animals served as their own controls by receiving cellulose or poly(allylamine/epichlorohydrin) in randomized order. The rats were fed ad libitum for three days to acclimate to the diet. Feces excreted during the next 48 hours were collected, lyophilized, and ground into powder. The inorganic phosphate content was determined according to the method of Taussky and Shorr: Microdetermination of Inorganic Phosphate. One gram of powdered feces was burned to remove carbon, then ashed in a 600° C. oven. Concentrated HCl was then added to dissolve the phosphorus. The phosphorus was determined with ferrous sulfate-ammonium molybdate reagent. Intensity of the blue color was determined at 700 nm on a Perkin-Elmer spectrophotometer through a 1 cm cell.

Figure 2:
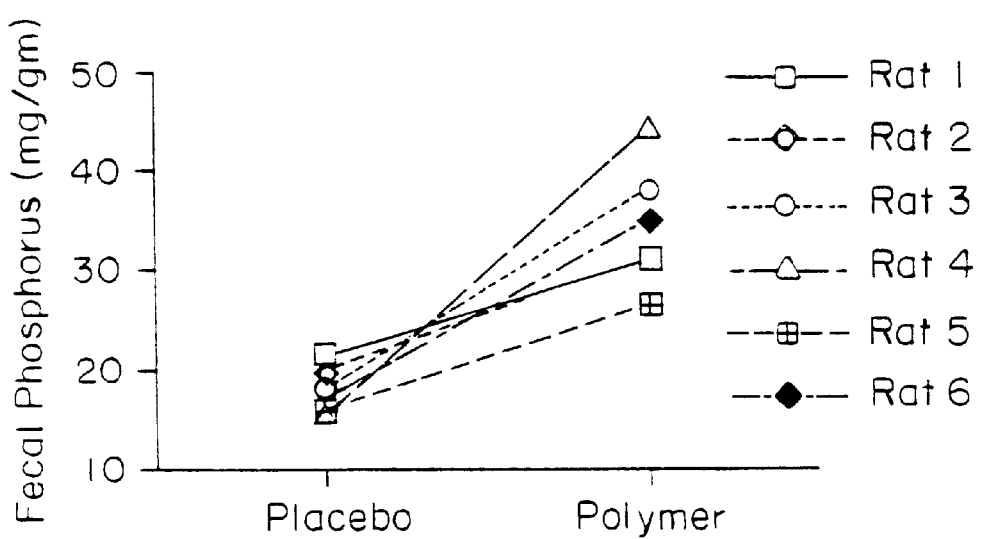
FIG. 2 is a graphic illustration of the phosphate concentration in fecal samples taken from rats fed with a dietary supplement of a crosslinked polyallylamine and micro-crystalline cellulose (placebo).

The results are shown in FIG. 2. Fecal phosphate concentration increased in all animals.

Urinary Phosphate Excretion in Partially Nephrectomized Rats

Sprague-Dawley rats, approximately 8 weeks old, were 75% nephrectomized. One kidney was surgically removed; approximately 50% of the renal artery flow to the contralateral kidney was ligated. The animals were fed a semi-purified rodent chow containing 0.385% inorganic phosphorus and either 10% poly(allylamine/epichlorohydrin) or cellulose. Urine was collected and analyzed for phosphate content on specific days. Absorbed dietary phosphate is excreted into the urine to maintain serum phosphate.

Figure 3:
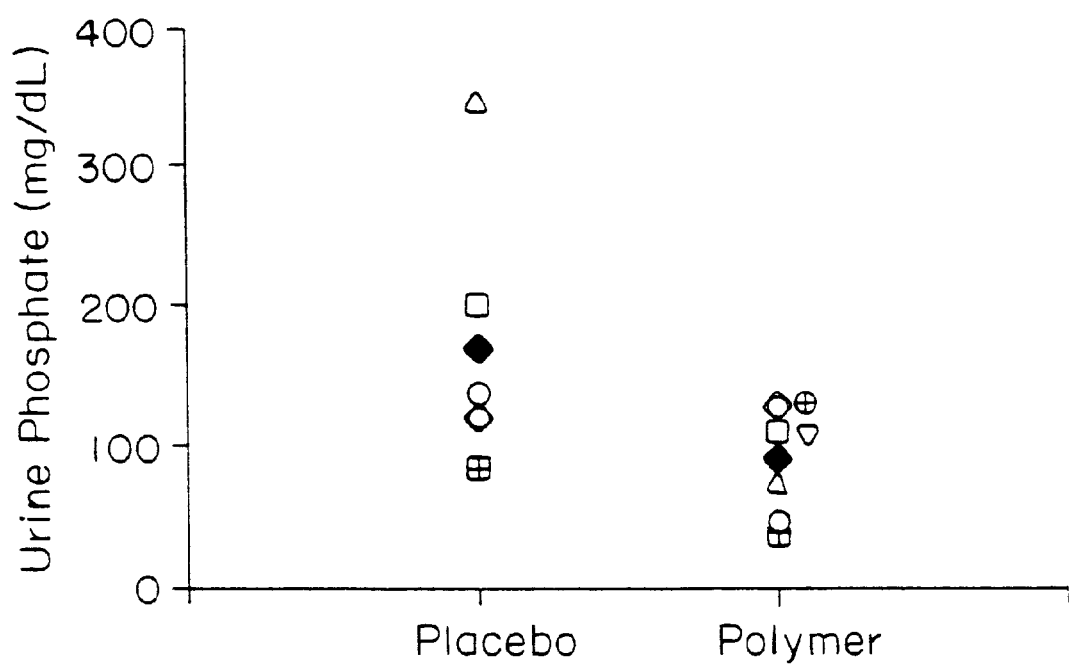
FIG. 3 is a graphic illustration of the urinary phosphate concentration in rats similarly given a dietary supplement of a crosslinked polyallylamine and micro-crystalline cellulose (placebo).

The results are shown in FIG. 3. None of the animals became hyperphosphatemic or uremic, indicating that the residual kidney function was adequate to filter the absorbed phosphate load. The animals receiving the poly (allylamine/epichlorohydrin) demonstrated a trend towards reduced phosphate excretion, indicative of reduced phosphate absorption.

SYNTHESES

Poly(allylamine hydrochloride)

To a 5 L, water jacketed reaction kettle equipped with 1) a condenser topped with a nitrogen gas inlet and 2) a thermometer and 3) a mechanical stirrer was added concentrated hydrochloric acid (2590 mL). The acid was cooled to 5° C. using circulating water in the jacket of the reaction kettle at 0° C. Allylamine (2362 mL; 1798 g) was added dropwise with stirring, maintaining a temperature of 5–10° C. After the addition was complete, 1338 mL of liquid was removed by vacuum distillation at 60–70° C. Azobis (amidinopropane) dihydrochloride (36 g) suspended in 81 mL water was added. The kettle was heated to 50° C. under a nitrogen atmosphere with stirring for 24 hours. Azobis (amidinopropane) dihydrochloride (36 g) suspended in 81 mL water was again added and the heating and stirring continued for an additional 44 hours. Distilled water (720 mL) was added and the solution allowed to cool with stirring. The liquid was added dropwise to a stirring solution of methanol (30 L). The solid was then removed by filtration, resuspended in methanol (30 L), stirred 1 hour, and collected by filtration. This methanol rinse was repeated once more and the solid was dried in a vacuum oven to yield 2691 g of a granular white solid (poly(allylamine hydrochloride).

Poly(allylamine/epichlorohydrin)

To a 5 gallon bucket was added poly(allylamine hydrochloride) (2.5 kg) and water 10 L). The mixture was stirred to dissolve and the pH was adjusted to 10 with a solid NaOH. The solution was allowed to cool to room temperature in the bucket and epichlorohydrin (250 mL) was added all at once with stirring. The mixture was stirred gently until it gelled after about 15 minutes. The gel was allowed to continue curing for 18 hours at room temperature. The gel was then removed and put into a blender with isopropanol (about 7.5 L). The gel was mixed in the blender with about 500 mL isopropanol for ~3 minutes to form coarse particles and the solid was then collected by filtration. The solid was rinsed three times by suspending it in 9 gallons of water, stirring the mixture for 1 hour, and collecting the solid by filtration. The solid was rinsed once by suspending it in isopropanol (60 L), stirring the mixture for 1 hour, and collecting the solid by filtration. The solid was dried in a vacuum oven for 18 hours to yield 1.55 Kg of a granular, brittle, white solid.

Poly(allylamine/butanedioldiglycidyl ether)

To a 5 gallon plastic bucket was added poly(allylamine hydrochloride) (500 g) and water (2 L). The mixture was stirred to dissolve and the pH was adjusted to 10 with solid NaOH (142.3 g). The solution was allowed to cool to room temperature in the bucket and 1,4-butanedioldiglycidyl ether (130 mL) was added all at once with stirring. The mixture was stirred gently until it gelled after 4 minutes. The gel was allowed to continue curing for 18 hours at room temperature. The gel was then removed and dried in a vacuum oven at 75° C. for 24 hours. The dry solid was ground and sieved for −30 mesh and then suspended in 6 gallons on water. After stirring for 1 hour the solid was filtered off and rinse process repeated twice more. The solid was rinsed twice in isopropanol (3 gallons), and dried in a vacuum oven at 50° C. for 24 hours to yield 580 g of a white solid.

Poly(allylamine/ethanedioldiglycidyl ether)

To a 100 mL beaker was added poly(allylamine hydrochloride) (10 g) and water (40 mL). The mixture was stirred to dissolve and the pH was adjusted to 10 with solid NaOH. The solution was allowed to cool to room temperature in the beaker and 1,2 ethanedioldiglycidyl ether (2.0 mL) was added all at once with stirring. The mixture was allowed to continue curing for 18 hours at room temperature. The gel was then removed and blended in 500 mL of methanol. The solid was filtered off and suspended in water (500 mL). After stirring for 1 hour the solid was filtered off and the rising process repeated. The solid was rinsed twice in isopropanol (400 mL), and dried in a vacuum oven at 50° C. for 24 hours to yield 8.7 g of a white solid.

Poly(allylamine/dimethylsuccinate)

To a 500 mL round bottom flask was added poly (allylamine hydrochloride) (10 g), methanol (100 mL), and triethylamine (10 mL). The mixture was stirred and dimethylsuccinate (1 mL) was added. The solution was heated to reflux and stirring turned off after 30 minutes. After 18 hours the solution was cooled to room temperature and solid was filtered off and suspended in water (1 L). After stirring for 1 hour the solid was filtered off and the rinse process repeated twice more. The solid was rinsed once in isopropanol (800 mL), and dried in a vacuum oven at 50° C. for 24 hours to yield 5.9 g of a white solid.

Poly(allyltrimethylammonium chloride)

To a 500 mL three necked flask equipped with a magnetic stirrer, a thermometer, and a condenser topped with a nitrogen inlet, was added poly(allylamine) crosslinked with epichlorohydrin (5.0 g), methanol (300 mL), methyl iodide (20 mL), and sodium carbonate (50 g). The mixture was then cooled and water was added to total volume of 2 L. Concentrated hydrochloric acid was added until no further bubbling resulted and the remaining solid was filtered off. The solid was rinsed twice in 10% aqueous NaCl (1 L) by stirring for 1 hour followed by filtration to recover the solid. The solid was then rinsed three times by suspending it in water (2 L), stirring for 1 hour, and filtering to recover the solid. Finally, the solid was rinsed as above in methanol and dried in a vacuum over at 50° C. for 18 hours to yield 7.7 g of white granular solid.

Poly(ethyleneimine)/acryloyl chloride

Into a 5 L three neck flask equipped with a mechanical stirrer, a thermometer, and an additional funnel was added polyethyleneimine (510 g of a 50% aqueous solution (equivalent to 255 g of dry polymer) and isopropanol (2.5 L). Acryloyl chloride (50 g) was added dropwise through the addition funnel over a 35 minute period, keeping the temperature below 29° C. The solution was then heated to 60° C. with stirring for 18 hours. The solution was cooled and solid immediately filtered off. The solid was rinsed three times by suspending it in water (2 gallons), stirring for 1 hour, and filtering to recover the solid. The solid was rinsed once by suspending it in methanol (2 gallons), stirring for 30 minutes, and filtering to recover the solid. Finally, the solid was rinsed as above in isopropanol and dried in a vacuum over at 50° C. for 18 hours to yield 206 g of light orange granular solid.

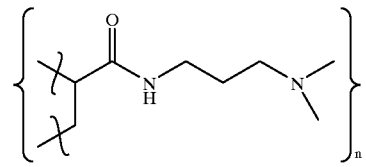

Poly(dimethylaminopropylacrylamide)

Dimethylamino-propylacrylamide (10 g) and methylenebisacrylamide (1.1 g) were dissolved in 50 mL of water in a 100 mL three neck flask. The solution was stirred under nitrogen for 10 minutes. Potassium persulfate (0.3 g) and sodium metabisulfite (0.3 g) were each dissolved in 2–3 mL of water and then mixed. After a few seconds this solution was added to the monomer solution, still under nitrogen. A gel formed immediately and was allowed to sit overnight. The gel was removed and blended with 500 mL of isopropanol. The solid was filtered off and rinsed three times with acetone. The solid white powder was filtered off and dried in a vacuum oven to yield 6.1 g.

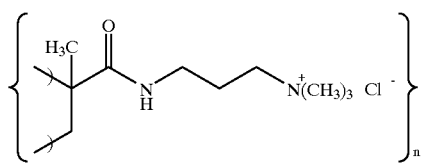

Poly(Methacrylamidopropyltrimethylammoniumchloride)= [Poly (MAPTAC)]

[3-(Methacryloylamino)propyl]trimethylammonium chloride (38 mL of 50% aqueous solution) and methylenebis-methacrylamide (2.2 g) were stirred in a beaker at room temperature. Methanol (10 mL was added and the solution was warmed to 40° C. to fully dissolve the bisacrylamide. Potassium persulfate (0.4 g) was added and the solution stirred for 2 minutes. Potassium metabisulfite (0.4 g) was added and stirring was continued. After 5 minutes the solution was put under a nitrogen atmosphere. After 20 minutes the solution contained significant precipitate and the solution was allowed to sit overnight. The solid was washed three times with isopropanol and collected by filtration. The solid was then suspended in water 500 (mL) and stirred for several hours before being collected by centrifugation. The solid was again washed with water and collected by filtration. The solid was then dried in a vacuum oven to yield 21.96 g.

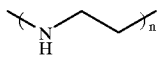

Poly(ethyleneimine) "A" Polyethyleneimine (50 g of a 50% aqueous solution; Scientific Polymer Products) was dissolved in water (100 mL). Epichlorohydrin (4.6 mL) was added dropwise. The solution was heated to 55° C. for 4 hours, after which it had gelled. The gel was removed, blended with water (1 L) and the solid was filtered off. It was resuspended in water (2 L) and stirred for 10 minutes. The solid was filtered off, the rinse repeated once with water and twice with isopropanol, and the resulting gel was dried in a vacuum oven to yield 26.3 g of a rubbery solid.

Poly(ethyleneimine) "B" and Poly(ethyleneimine) "C" were made in a similar manner, except using 9.2 and 2.3 mL of epichlorohydrin, respectively.

Poly(methylmethacrylate-co-divinylbenzene)

Methylmethacrylate (50 g) and divinylbenzene (5 g) and azobisisobutyronitrile (1.0 g) were dissolved in isopropanol (500 mL) and heated to reflux for 18 hours under a nitrogen atmosphere. The solid white precipitate was filtered off, rinsed once in acetone (collected by centrifugation), once in water (collected by filtration and dried in a vacuum oven to yield 19.4 g.

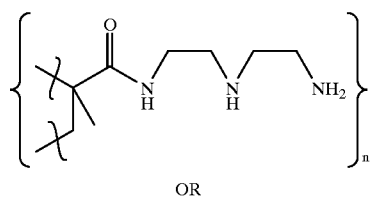

OR

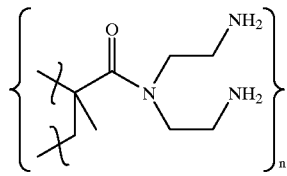

Poly(diethylenetriaminemethacrylamide)

Poly(methylmethacrylate-co-divinylbenzene) (20 g) was suspended in diethylenetriamine (200 mL) and heated to reflux under a nitrogen atmosphere for 18 hours. The solid was collected by filtration, resuspended in water (500 mL), stirred 30 minutes, filtered off, resuspended in water (500 mL), stirred 30 minutes, filtered off, rinsed briefly in isopropanol, and dried in a vacuum oven to yield 18.0 g.

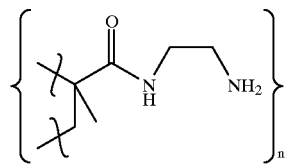

Poly(pentaethylenehexaminemethacrylamide), Poly(tetraethylenepentaminemethacrylamide), and Poly(triethylenetetraaminemethacrylamide) were made in a manner similar to poly(diethylenetriaminemethacrylamide) from pentaethylenehexamine, tetraethylenepentamine, and triethylenetetraamine, respectively.

Poly(methylmethacrylate/PEI)

Poly(methylmethacrylate-co-divinylbenzene) (1.0 g) was added to a mixture containing hexanol (9150 mL) and polyethyleneimine (15 g in 15 g water). The mixture was heated to reflux under nitrogen for 4 days. The reaction was cooled and the solid was filtered off, suspended in methanol (300 mL), stirred 1 hour, and filtered off. The rinse was repeated once with isopropanol and the solid was dried in a vacuum oven to yield 0.71 g.

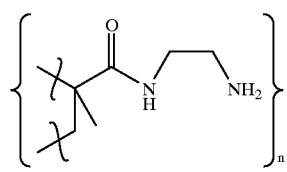

Poly(aminoethylmethacrylamide)

Poly(methylmethacrylate-co-divinylbenzene) (20 g) was suspended in ethylenediamine 9200 mL) and heated to reflux under a nitrogen atmosphere for 3 days. The solid was collected by centrifugation, washed by resuspending it in water (500 mL), stirring for 30 minutes, and filtering off the solid. The solid was washed twice more in water, once in isopropanol, and dried in a vacuum oven to yield 17.3 g.

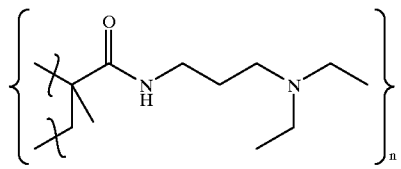

Poly(diethylaminopropylmethacrylamide)

Poly(methylmethacrylate-co-divinylbenzene) (20 g) was suspended in diethylaminopropylamine (200 mL) and heated to reflux under a nitrogen atmosphere for 18 hours. The solid was collected by filtration, resuspended in water (500 mL), filtered off, resuspended in water (500 mL), collected by filtration, rinsed briefly in isopropanol, and dried in a vacuum oven to yield 8.2 g.

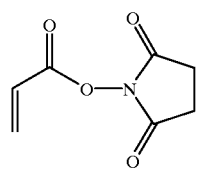

NHS-acrylate

N-Hydroxysuccinimide (NHS, 157.5 g) was dissolved in chloroform (2300 mL) in a 5 L flask. The solution was cooled to 0° C. and acryloyl chloride (132 g) was added dropwise, keeping the temperature 20° C. After addition was complete, the solution was stirred for 1.5 hours, rinsed with water (1100 mL) in a separatory funnel and dried over anhydrous sodium sulfate. The solvent was removed under vacuum and a small amount of ethyl acetate was added to the residue. This mixture was poured into hexane (200 mL) with stirring. The solution was heated to reflux, adding more ethyl acetate (400 mL). The insoluble NHS was filtered off, hexane (1 L) was added, the solution was heated to reflux, ethyl acetate (400 mL) was added, and the solution allowed to cool to <10° C. The solid was then filtered off and dried in a vacuum oven to yield 125.9 g. A second crop of 80 g was subsequently collected by further cooling.

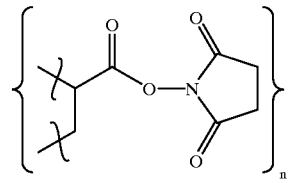

Poly(NHS-acrylate)

NHS-acrylate (28.5 g), methylenebisacrylamide (1.5 g) and tetrahydrofuran (500 mL) were mixed in a 1 L flask and heated to 50° C. under a nitrogen atmosphere. Azobisisobutyronitrile (0.2 g) was added, the solution was stirred for 1 hour, filtered to remove excess N-hydroxysuccinimide, and heated to 50° C. for 4.5 hours under a nitrogen atmosphere. The solution was then cooled and the solid was filtered off, rinsed in tetrahydrofuran, and dried in a vacuum oven to yield 16.1 g.

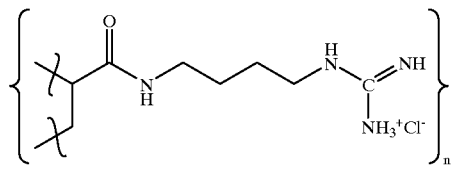

Poly(quanidinobutylacrylamide)

Poly(NHS-acrylate) (1.5 g) was suspended in water (25 mL) containing agmatine (1.5 g) which had been adjusted to pH 9 with solid NaOH. The solution was stirred for 4 days, after which time the pH had dropped to 6.3. Water was added to a total of 500 mL, the solution was stirred for 30 minutes and the solid was filtered off. The solid was rinsed twice in water, twice in isopropanol, and dried in a vacuum oven to yield 0.45 g.

Poly(methacryloyl chloride)

Methacryloyl chloride (20 mL), divinyl benzene (4 mL of 80% purity), AIBN (0.4 g), and THF (150 mL) were stirred at 60° C. under a nitrogen atmosphere for 18 hours. The solution was cooled and the solid was filtered off, rinsed in THF, then acetone, and dried in a vacuum oven to yield 8.1 g.

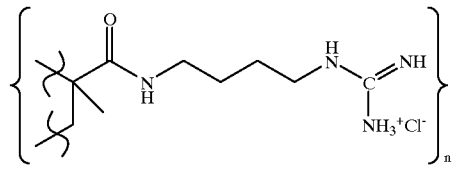

Poly(guanidinobutylmethacrylamide)

Poly(methacryloyl chloride) (0.5 g), agmatine sulfate (1.0 g), triethylamine (2.5 mL), and acetone (50 mL) were stirred together for 4 days. Water (100 mL) was added and the mixture stirred for 6 hours. The solid was filtered off and washed by resuspending in water (500 mL), stirring for 30 minutes, and filtering off the solid. The wash was repeated twice in water, once in methanol, and the solid was dried in a vacuum oven to yield 0.41 g.

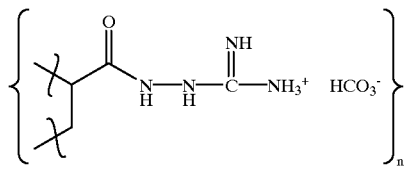

Poly(guanidinoacrylamide)

The procedure for poly(guanidinobutylacrylamide) was followed substituting aminoguanidine bicarbonate (5.0 g) for the agmatine, yielding 0.75 g.

Poly(PEH/EPI)

Epichlorohydrin (1.5 g) was added dropwise to a solution containing pentaethylenehexamine (20 g) and water (100 mL), keeping the temperature between 65° C. The solution was stirred until it gelled and heating was continued for 4 hours (at 65° C.). After sitting overnight at room temperature the gel was removed and blended with water (1 L). The solid was filtered off, water was added (1 L), and the blending and filtration were repeated. The gel was suspended in isopropanol and the resulting solid was collected by filtration and dried in a vacuum oven to yield 28.2 g.

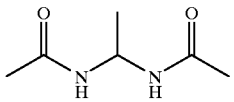

Ethylidenebisacetamide

Acetamide (118 g), acetaldehyde (44.06 g), copper acetate (0.2 g), and water (300 mL) were placed in a 1 L three neck flask fitted with condenser, thermometer, and mechanical stirred. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and stirred for a few minutes after which the solid was filtered off and discarded. The acetone was cooled to 0° C. and solid was filtered off. This solid was rinsed in 500 mL acetone and air dried 18 hours to yield 31.5 g.

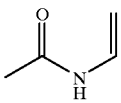

Vinylacetamide

Ethylidenebisacetamide (31.05), calcium carbonate (2 g) and celite 541 (2 g) were placed in a 500 mL three neck flask fitted with a thermometer, a mechanical stirrer, and a distilling head atop a vigroux column. The mixture was vacuum distilled at 35 mm Hg by heating the pot to 180–225° C. Only a single fraction was collected (10.8 g) which contained a large portion of acetamide in addition to the product (determined by NMR). This solid product was dissolved in isopropanol (30 mL) to form the crude solution used for polymerization.

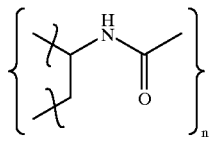

Poly(vinylacetamide)

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven to yield 0.8 g.

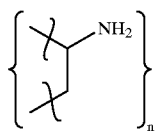

Poly(vinylamine)

Poly(vinylacetamide) (0.79 g) was placed in a 100 mL one neck flask containing water 25 mL and concentrated HCl 25 mL. The mixture was refluxed for 5 days, the solid was filtered off, rinsed once in water, twice in isopropanol, and dried in a vacuum oven to yield 0.77 g. The product of this reaction (~0.84 g) was suspended in NaOH (46 g) and water (46 g) and heated to boiling (~140° C. ). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then the isopropanol, and dried in a vacuum oven to yield 0.51 g.

Poly(trimethylammoniomethylstyrene chloride) is the copolymer of trimethylammoniomethylstyrene chloride and divinyl benzene.

Poly(DET/EPI) is the polymer formed by reaction of diethylenetriamine and epichlorohydrin.

Poly(ethyleneimine) Salts

Polyethyleneimine (25 g dissolved in 25 g water) was dissolved in water (100 mL) and mixed with toluene (1 L). Epichlorohydrin (2.3 mL) was added and the mixture heated to 60° C. with vigorous mechanical stirring for 18 hours. The mixture was cooled and the solid filtered off, resuspended in methanol (2 L), stirred 1 hour, and collected by centrifugation. The solid was suspended in water (2 L), stirred 1 hour, filtered off, suspended in water (4 L), stirred 1 hour, and again filtered off. The solid was suspended in acetone (4 L) and stirred 15 minutes, the liquid was poured off, acetone (2 L) was added, the mixture was stirred 15 minutes, the acetone was again poured off, and the solid was dried in a vacuum oven to form intermediate "D".

Poly(ethyleneimine sulfate A)

Intermediate "D" (1.0 g) was suspended in water (150 mL), stirred 30 minutes, and partially neutralized with sulfuric acid (1.1 g). The mixture was stirred an additional 30 minutes, the solid was filtered off, resuspended in methanol (200 mL), stirred 5 minutes, filtered off, and dried in a vacuum oven.

Poly(ethyleneimine sulfate B)

Intermediate "D" (1.0 g) was suspended in water (150 mL), stirred 30 minutes, and partially neutralized with sulfuric acid (0.57 g). The mixture was stirred an additional 30 minutes, the solid was filtered off, resuspended in methanol (200 mL), stirred 5 minutes, filtered off, and dried in a vacuum oven.

Poly(ethyleneimine sulfate C)

Intermediate "D" (1.0 g) was suspended in water (150 mL), stirred 30 minutes, and partially neutralized with sulfuric acid (0.28 g). The mixture was stirred an additional 30 minutes, the solid was filtered off, resuspended in methanol (200 mL), stirred 5 minutes, filtered off, and dried in a vacuum oven.

Poly(ethyleneimine sulfate D)

Intermediate "D" (1.0 g) was suspended in water (150 mL), stirred 30 minutes, and partially neutralized with sulfuric acid (0.11 g). The mixture was stirred an additional 30 minutes, the solid was filtered off, resuspended in methanol (200 mL), stirred 5 minutes, filtered off, and dried in a vacuum oven.

Poly(ethyleneimine tartrate A)

Intermediate "D" (1.0 g) was suspended in water (150 mL), stirred 30 minutes, and partially neutralized with tartaric acid (1.72 g). The mixture was stirred an additional 30 minutes, the solid was filtered off, resuspended in methanol (200 mL), stirred 5 minutes, filtered off, and dried in a vacuum oven.

Poly(ethyleneimine tartrate B)

Intermediate "D" (1.0 g) was suspended in water (150 mL), stirred 30 minutes, and partially neutralized with tartaric acid (0.86 g). The mixture was stirred an additional 30 minutes, the solid was filtered off, resuspended in methanol (200 mL), stirred 5 minutes, filtered off, and dried in a vacuum oven.

Poly(ethyleneimine tartrate C)

Intermediate "D" (1.0 g) was suspended in water (150 mL), stirred 30 minutes, and partially neutralized with tartaric acid (0.43 g). The mixture was stirred an additional 30 minutes, the solid was filtered off, resuspended in methanol (200 mL), stirred 5 minutes, filtered off, and dried in a vacuum oven.

Poly(ethyleneimine ascorbate A)

Intermediate "D" (1.0 g) was suspended in water (150 mL), stirred 30 minutes, and partially neutralized with ascorbic acid (4.05 g). The mixture was stirred an additional 30 minutes, the solid was filtered off, resuspended in methanol (200 mL), stirred 5 minutes, filtered off, and dried in a vacuum oven.

Poly(ethyleneimine ascorbate B)

Intermediate "D" (1.0 g) was suspended in water (150 mL), stirred 30 minutes, and partially neutralized with ascorbic acid (2.02 g). The mixture was stirred an additional 30 minutes, the solid was filtered off, resuspended in methanol (200 mL), stirred 5 minutes, filtered off, and dried in a vacuum oven.

Poly(ethyleneimine ascorbate C)

Intermediate "D" (1.0 g) was suspended in water (150 mL), stirred 30 minutes, and partially neutralized with ascorbic acid (1.01 g). The mixture was stirred an additional 30 minutes, the solid was filtered off, resuspended in methanol (200 mL), stirred 5 minutes, filtered off, and dried in a vacuum oven.

Poly(ethyleneimine citrate A)

Intermediate "D" (1.0 g) was suspended in water (150 mL), stirred 30 minutes, and partially neutralized with citric acid (1.47 g). The mixture was stirred an additional 30 minutes, the solid was filtered off, resuspended in methanol (200 mL), stirred 5 minutes, filtered off, and dried in a vacuum oven.

Poly(ethyleneimine citrate B)

Intermediate "D" (1.0 g) was suspended in water (150 mL), stirred 30 minutes, and partially neutralized with citric acid (0.74 g). The mixture was stirred an additional 30 minutes, the solid was filtered off, resuspended in methanol (200 mL), stirred 5 minutes, filtered off, and dried in a vacuum oven.

Poly(ethyleneimine citrate C)

Intermediate "D" (1.0 g) was suspended in water (150 mL), stirred 30 minutes, and partially neutralized with citric acid (0.37 g). The mixture was stirred an additional 30 minutes, the solid was filtered off, resuspended in methanol (200 mL), stirred 5 minutes, filtered off, and dried in a vacuum oven.

Poly(ethyleneimine succinate A)

Intermediate "D" (1.0 g) was suspended in water (150 mL), stirred 30 minutes, and partially neutralized with succinic acid (1.36 g). The mixture was stirred an additional 30 minutes, the solid was filtered off, resuspended in methanol (200 mL), stirred 5 minutes, filtered off, and dried in a vacuum oven.

Poly(ethyleneimine succinate B)

Intermediate "D" (1.0 g) was suspended in water (150 mL), stirred 30 minutes, and partially neutralized with succinic acid (0.68 g). The mixture was stirred an additional 30 minutes, the solid was filtered off, resuspended in methanol (200 mL), stirred 5 minutes, filtered off, and dried in a vacuum oven.

Poly(ethyleneimine chloride)

Polyethyleneimine (100 g in 100 g water) was dissolved in water (640 mL additional) and the pH was adjusted to 10 with concentrated HCl. Isopropanol (1.6 L) was added, followed by epichlorohydrin (19.2 mL). The mixture was stirred under nitrogen for 18 hours at 60° C. The solids were filtered off and rinsed with methanol (300 mL) on the funnel. The solid was rinsed by resuspending it in methanol (4 L), stirring 30 minutes, and filtering off the solid. The rinse was repeated twice with methanol, followed by resuspension in water (1 gallon). The pH was adjusted to 1.0 with concentrated HCl, the solid was filtered off, resuspended in water (1 gallon), the pH again adjusted to 1.0 with concentrated HCl, the mixture stirred 30 minutes, and the solid filtered off. The methanol rinse was again repeated and the solid dried in a vacuum oven to yield 112.4 g.

Poly(dimethylethyleneimine chloride)

Poly(ethyleneimine chloride) (5.0 g) was suspended in methanol (300 mL) and sodium carbonate (50 g) was added. Methyl iodide (20 mL) was added and the mixture heated to reflux for 3 days. Water was added to reach a total volume of 500 mL, the mixture stirred for 15 minutes, and the solid filtered off. The solid was suspended in water (500 mL), stirred 30 minutes, and filtered. The solid was suspended in water (1 L), the pH adjusted to 7.0 with concentrated HCl, and the mixture stirred for 10 minutes. The solid was filtered off, resuspended in isopropanol (1 L), stirred 30 minutes, filtered off, and dried in a vacuum oven to yield 6.33 g.

Use

The methods of the invention involve treatment of patients with hyperphosphatemia. Elevated serum phosphate is commonly present in patients with renal insufficiency, hypoparathyroidism, pseudohypoparathyroidism, acute untreated acromegaly, overmedication with phosphate salts, and acute tissue destruction as occurs during rhabdomyolysis and treatment of malignancies.

The term "patient" used herein is taken to mean any mammalian patient to which phosphate binders may be administered. Patients specifically intended for treatment with the methods of the invention include humans, as well as nonhuman primates, sheep, horses, cattle, goats, pigs, dogs, cats, rabbits, guinea pigs, hamsters, gerbils, rats and mice.

The compositions utilized in the methods of the inventions are orally administered in therapeutically effective amounts. Further, the polymer are preferably non-toxic and stable upon administration. A therapeutically effective amount of compound is that amount which produces a result or exerts an influence on the particular condition being treated. As used herein, a therapeutically effective amount of a phosphate binder means an amount which is effective in decreasing the serum phosphate levels of the patient to which it is administered.

By "non-toxic" it is meant that when ingested in therapeutically effective amounts neither the polymers nor any ions released into the body upon ion exchange are harmful or are substantially harmful.

By "stable" it is meant that when ingested in therapeutically effective amounts the polymers do not dissolve or otherwise decompose to form potentially harmful by-products, and remain substantially intact so that they can transport bound phosphate out of the body.

The present pharmaceutical compositions are generally prepared by known procedures using well known and readily available ingredients. In making the compositions of the present invention, the polymeric phosphate binder may be present alone, may be admixed with a carrier, diluted by a carrier, or enclosed within a carrier which may be in the form of a capsule, sachet, paper or other container. When the carrier serves as a diluent, it may be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carrier, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc.

It should be understood, however, that the foregoing description of the invention is intended merely to be illustrative by way of example only and than other modifications, embodiments, and equivalents may be apparent to those skilled in the art without departing from its spirit.

What is claimed is:

1. A method of making a pharmaceutical composition comprising cross-linked polyallylamine, said method comprising the steps of:
   (a) contacting poly(allylamine) with a difunctional crosslinking agent in an aqueous alkaline solution, said cross-linking agent being present in an amount sufficient for forming a poly(allylamine) gel, thereby producing an aqueous alkaline solution comprising polyallylamine and the cross-linking agent;
   (b) maintaining the aqueous alkaline solution comprising polyallylamine and the cross-linking agent at room temperature for a sufficient period of time for cross-linking of the poly(allylamine), thereby forming cross-linked polyallylamine gel;
   (c) washing the cross-linked polyallylamine with water; and
   (d) at least one step selected from the group consisting of:
      (i) admixing the cross-linked polyallylamine with a pharmaceutically acceptable carrier, excipient or diluent; and
      (ii) enclosing the cross-linked polyallylamine within a pharmaceutically acceptable carrier.

2. The method of claim 1 wherein the difunctional cross-linking agent is selected from the group consisting of succinyl dichloride, bisphenol A diglycidyl ether, pyromellitic dianhydride, toluene diisocyanate, 1,4-butanedioldiglycidyl ether, 1,2 ethanedioldiglycidyl ether, 1,3-dichloropropane, 1,2-dichloroethane, 1,3-dibromopropane, 1,2-dibromoethane, succinyl dichloride, dimethylsuccinate and acryloyl chloride.

3. The method of claim 1 wherein the difunctional cross-linking agent is epichlorohydrin.

4. The method of claim 1 wherein the alkaline aqueous solution of poly(allylamine) is prepared by adding base to an aqueous solution of an acid salt of poly(allylamine).

5. The method of claim 4 wherein the acid salt of poly(allylamine) is the hydrochloride salt of poly(allylamine).

6. The method of claim 4 wherein the base is sodium hydroxide or potassium hydroxide.

7. The method of claim 4 wherein the alkaline aqueous solution has a pH of about 10.

8. The method of claim 1, further comprising the step of fragmenting the gel to form gel particles.

* * * * *